US 9,111,372 B2

(12) United States Patent
Ortega et al.

(10) Patent No.: US 9,111,372 B2
(45) Date of Patent: Aug. 18, 2015

(54) SYSTEM AND METHOD FOR OBJECT IDENTIFICATION AND ANOMALY DETECTION

(75) Inventors: Mireya Ortega, South Lake Tahoe, CA (US); Roger Daugherty, Los Angeles, CA (US)

(73) Assignee: VISIONARY TECHNOLOGIES, INC., South Lake Tahoe, CA (US)

( * ) Notice: Subject to any disclaimer, the term of this patent is extended or adjusted under 35 U.S.C. 154(b) by 1014 days.

(21) Appl. No.: 11/890,533

(22) Filed: Aug. 6, 2007

(65) Prior Publication Data

US 2009/0129639 A1 May 21, 2009

Related U.S. Application Data

(60) Provisional application No. 60/837,311, filed on Aug. 11, 2006.

(51) Int. Cl.
*G06K 9/00* (2006.01)
*A61B 6/14* (2006.01)
*G06T 19/00* (2011.01)
*G06T 7/00* (2006.01)

(52) U.S. Cl.
CPC .............. *G06T 19/00* (2013.01); *G06T 7/0012* (2013.01); *A61B 6/14* (2013.01); *G06K 2209/05* (2013.01); *G06T 2200/24* (2013.01); *G06T 2207/10072* (2013.01); *G06T 2207/30036* (2013.01)

(58) Field of Classification Search
None
See application file for complete search history.

(56) References Cited

U.S. PATENT DOCUMENTS

| | | | |
|---|---|---|---|
| 7,373,286 B2 | 5/2008 | Nikolskiy et al. | |
| 7,636,461 B2 * | 12/2009 | Spies et al. | 382/128 |
| 7,826,646 B2 * | 11/2010 | Pavlovskaia et al. | 382/128 |
| 7,840,042 B2 | 11/2010 | Kriveshko et al. | |
| 8,021,147 B2 | 9/2011 | Sporbert et al. | |
| 2002/0176619 A1 | 11/2002 | Love | |
| 2004/0029068 A1 | 2/2004 | Sachdeva et al. | |
| 2005/0089822 A1 | 4/2005 | Geng | |
| 2006/0008050 A1 * | 1/2006 | Massie | 378/38 |
| 2007/0099147 A1 | 5/2007 | Sachdeva et al. | |
| 2007/0207437 A1 | 9/2007 | Sachdeva et al. | |
| 2008/0051650 A1 * | 2/2008 | Massie et al. | 600/425 |
| 2009/0061381 A1 | 3/2009 | Durbin et al. | |
| 2013/0295524 A1 * | 11/2013 | Colby | 433/215 |

* cited by examiner

*Primary Examiner* — Kim Vu
*Assistant Examiner* — Fred Hu
(74) *Attorney, Agent, or Firm* — Michael A. Kerr; Kerr IP Group, LLC

(57) ABSTRACT

A system for identifying dental objects, visualizing a dental image, and method for identifying dental anomalies are described. The system for identifying dental objects comprises a 3-D dental image, a database, a digital processing component, and an interactive graphical user interface is described. The 3-D dental image is generated by a medical imaging device. The database has data fields that include locations for teeth, locations for each section of tooth, standard shapes associated with individual teeth, standard shapes associated with each of the sections of tooth, and bone density data for each section of tooth. The digital processing component is configured to process the 3-D image and is in operative communication with the database. The digital processing component is configured to identify an object by combining a plurality of voxels having a common density and tagging the object. The interactive graphical user interface (GUI) permits the user to interact with the object.

16 Claims, 15 Drawing Sheets

SYSTEM AND METHOD FOR OBJECT IDENTIFICATION AND ANOMALY DETECTION

CROSS-REFERENCE TO RELATED APPLICATIONS

This application claims benefit under 35 U.S.C. 119(e) of U.S. Provisional Application No. 60/837,311, filed Aug. 11, 2006, which is incorporated herein by reference in its entirety.

BACKGROUND

1. Field of Invention

The invention is related to analyzing three dimensional (3-D) images. More particularly, the invention is related to systems and methods for identifying objects associated with the 3-D images.

2. Description of Related Art

Generally, dental images are displayed in two-dimensions using light tables, e.g. X-rays. These two dimensional views provide a single perspective of the image. Three-dimensional (3-D) imaging systems have also been developed. These systems provide high-definition digital imaging with relatively short scan times, e.g. 20 seconds. The image reconstruction takes less than two minutes. The X-ray source is typically a high frequency source with a cone x-ray beam, and employs an image detector with an amorphous silicon flat panel. The images are 12-bit gray scale and may have a voxel size of 0.4 mm to 0.1 mm. Image acquisition is performed in a single session and is based on a 360 degree rotation of the X-ray source. The output data are digital images that are stored using conventional imaging formats such as the Digital Imaging and Communications in Medicine (DICOM) standard.

The 3-D volumetric imaging system provides complete views of oral and maxillofacial structures. The volumetric images provide complete 3-D views of anatomy for a more thorough analysis of bone structure and tooth orientation. These 3-D images are frequently used for implant and oral surgery, orthodontics, and TMJ analysis. There are a variety of different software solutions that can be integrated into the 3-D dental imaging systems. These third party solutions are generally related to implant planning, and assist in planning and placement of the implants. Additionally, the 3-D dental images can be used for developing models to assist in planning an operation.

In spite of the advances in the 3-D imaging systems and the 3-D imaging software, the software techniques for visualization of the dental images do not provide a dentist with sufficient flexibility to manipulate the 3-D image. Additionally, the visualization features provided by current third party solutions lack the ability to detect objects, detect irregularities, and detect anomalies.

SUMMARY

A system for identifying dental objects comprising a 3-D dental image, a database, a digital processing component, and an interactive graphical user interface is described. The 3-D dental image is generated by a medical imaging device. The database has data fields that include locations for teeth, locations for each section of tooth, standard shapes associated with individual teeth, standard shapes associated with each of the sections of tooth, and bone density data for each section of tooth. The digital processing component is configured to process the 3-D image and is in operative communication with the database. The digital processing component is configured to identify an object by combining a plurality of voxels having a common density and tagging the object. The interactive graphical user interface (GUI) permits the user to interact with the object.

A method for visualizing a dental image is described. The method comprises receiving a plurality of high resolution 3-D dental data associated with a patient's mouth that is generated using computed tomography. The method then proceeds to convert the high resolution dental data into an image comprised of a plurality of cubic voxels. The location for each cubic voxel and degree of attenuation for each voxel is identified. The degree of attenuation for each voxel is then associated with a particular common bone density. A plurality of dental objects are then generated, in which each dental object is generated by combining voxels having one of the common bone densities. The method then proceeds to determine the boundaries for each dental object and compares each dental object to a standard shape to confirm identification of each dental object. Each of the objects is then tagged so that one or more objects may be combined.

A method for identifying anomalies in a scanned 3-D dental image is also described. The method comprises providing a database having data fields related to location for teeth, locations for each section of tooth, standard shapes associated with the teeth, standard shapes associated with each of the sections of tooth, and a bone density data for each section of tooth. A 3-D image having a plurality of cubic voxels is generated and the location for each voxel is identified. The method then proceeds to identify the signal strength for each cubic voxel and associates the signal strength for each voxel with the bone density data. A first object is then generated by combining a first grouping of voxels having a first bone density and the first object is compared to data in the database. Anomalies are identified after comparing the first object to one or more fields in the database.

BRIEF DESCRIPTION OF THE DRAWINGS

Embodiments for the following description are shown in the following drawings.

DESCRIPTION

Figure 1A:
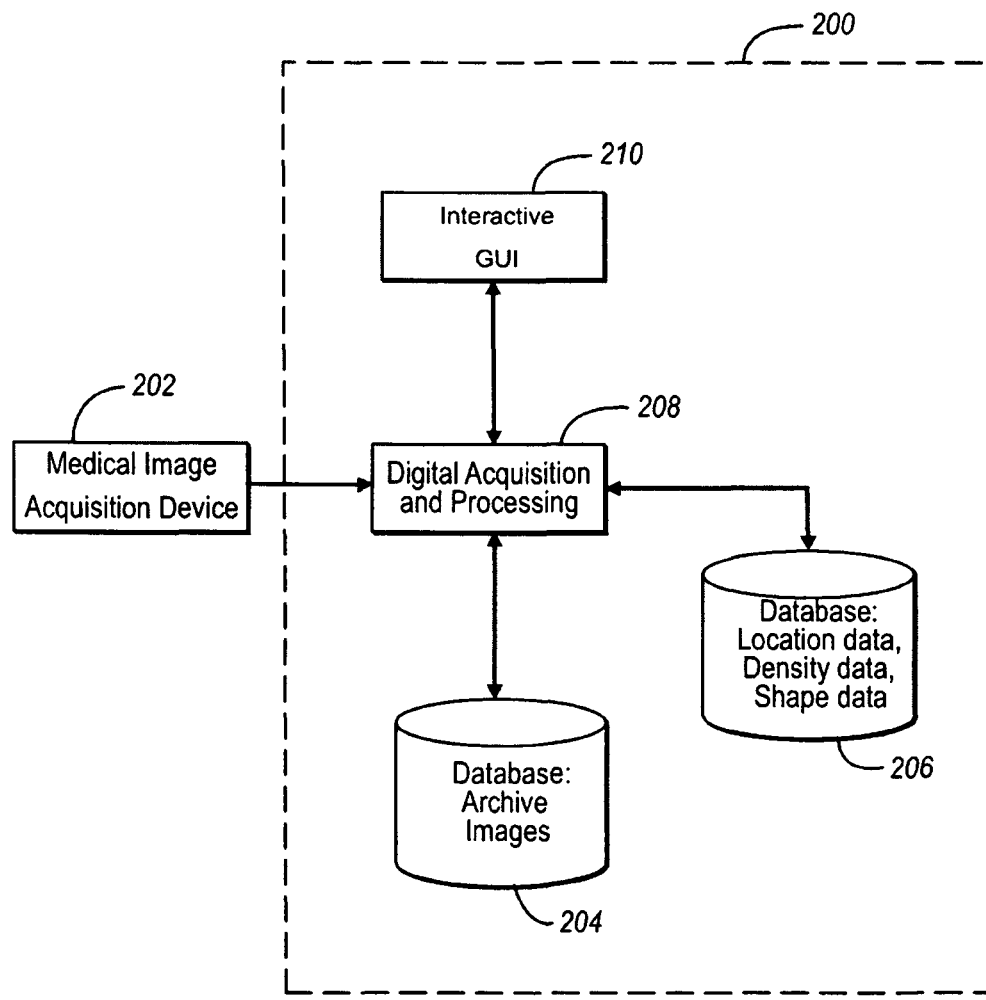
FIG. 1A is shows an illustrative system overview.

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural, logical and electrical changes may be made without departing from the spirit and scope of the claims. The following detailed description is, therefore, not to be taken in a limited sense.

Note, the leading digit(s) of the reference numbers in the Figures correspond to the figure number, with the exception that identical components which appear in multiple figures are identified by the same reference numbers.

The systems and methods described herein are generally related to visualization tools that operate with 3-D images generated using tomography. Tomography is imaging by sections or sectioning. The mathematical procedures for imaging are referred to as tomographic reconstruction. Imaging is the process of creating a virtual image of a physical object, its detailed structure, its substructure or any combination thereof. Those skilled in the art shall appreciate that tomographic imaging includes analyzing the attenuation of the captured image using the Radon transform and filtered back projection. There are a variety of different types of tomography including but not limited to Atom Probe Tomography, Computed Tomography, Electrical Impedance Tomography, Magnetic Resonance Tomography, Optical Coherence Tomography, Positron Emission Tomography, Quantum Tomography, Single Photon Emission Computed Tomography, and X-Ray Tomography. Attenuation refers to any reduction in signal strength.

The systems and methods described herein allow improved visualization, object identification, anomaly detection, and predictive growth rate features. Visualization refers to the process of taking one or more images and incorporates a comprehension of the physical relationship or significance of the features contained in the images. An object is a physical relationship within an image that is capable of being grasped through visualization and an object is comprised of a plurality of voxels that presume a common basis. A variety of techniques, methods, algorithms, mathematical formulae, or any combination thereof may be used to identify a common basis. In the illustrative examples, elements such as location, bone density, shape or a combination thereof may be used to identify at least one common basis that is used for object identification. Bone density is the measure of mass of bone in relation to volume. Therefore, one or more common basis may be used for object identification.

It shall be appreciated by those of ordinary skill in the art that the systems and methods described herein can be applied to a plurality of different modalities. A modality in a medical image is any of the various types of equipment or probes used to acquire images of the body. Magnetic Resonance Imaging is an example of a modality in this context.

Referring to FIG. 1A there is shown an illustrative system. The illustrative system 200 receives a 3-D dental image 202 that is stored in a first database 204 that stores archived images. A digital acquisition and processing component 208 processes received 3-D dental images. Particular information that is used to process the 3-D dental images is stored in the second database 206. An interactive graphical user interface 210 permits a user to manipulate the processed images and to interact with each illustrative dental object. By way of example and not of limitations, the 3-D dental image is generated by a medical imaging device such as an i-CAT 3-D Imaging System from Imaging Sciences International.

The databases 204 and 206 comprise a plurality of data fields including, but not limited to, data fields that correspond to the location for a plurality of teeth, a plurality of locations for each section of tooth, a plurality of standard shapes associated with each tooth, a plurality of standard shapes associated with each of the sections of tooth, and a plurality of bone density data for each section of tooth.

The digital processing component 208 is configured to process the 3-D image, and is in operative communication with the database. The digital processing component is configured to provide improved visualization of the medical image. The digital processing component 208 is configured to identify an object by combining a plurality of voxels having a common density and tagging the object using the methods described herein. A voxel is a volume element that represents a value in 3-D space. Common density is a density associated with a particular object in an image, in which a degree of attenuation within the image is associated with density.

Additionally, the digital processing component 208 is also configured to permit modifying the shape of at least one object. Furthermore, the digital processing component 208 is configured to provide a method for detecting anomalies and mathematically modeling growth rates.

Figure 1B:
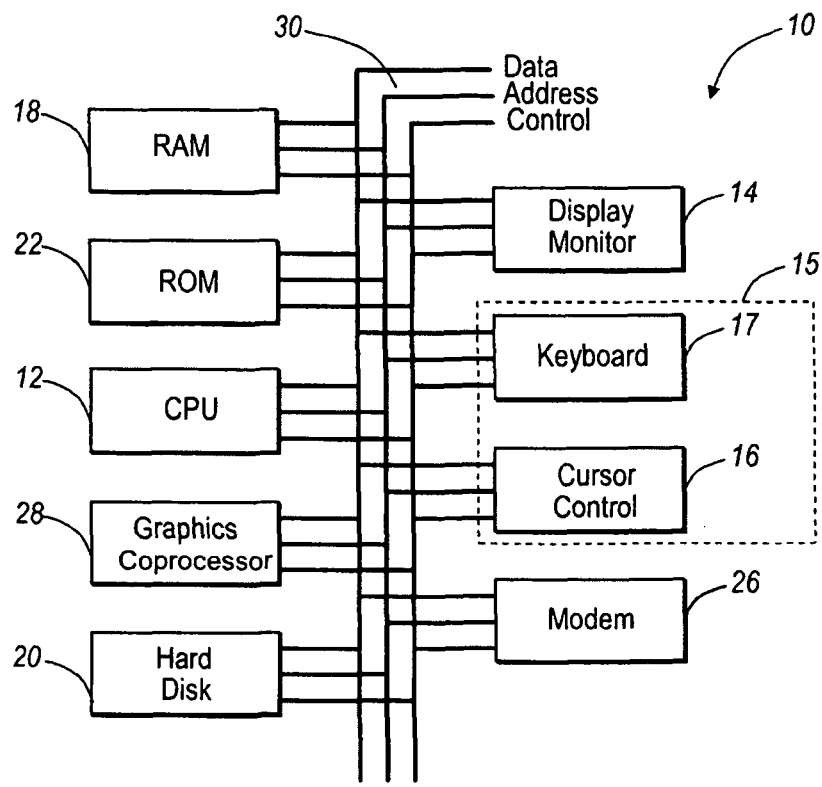
FIG. 1B is an illustrative general purpose computer.

In one embodiment the digital processing component 208 is a computer having a processor as shown in FIG. 1B. The illustrative general purpose computer 10 is suitable for implementing the systems and methods described herein. The general purpose computer 10 includes at least one central processing unit (CPU) 12, a display such as monitor 14, and an input device 15 such as cursor control device 16 or keyboard 17. The cursor control device 16 can be implemented as a mouse, a joy stick, a series of buttons, or any other input device which allows user to control the position of a cursor or pointer on the display monitor 14. Another illustrative input device is the keyboard 17. The general purpose computer may also include random access memory (RAM) 18, hard drive storage 20, read-only memory (ROM) 22, a modem 26 and a graphic co-processor 28. All of the elements of the general purpose computer 10 may be tied together by a common bus 30 for transporting data between the various elements.

The bus 30 typically includes data, address, and control signals. Although the general purpose computer 10 illustrated in FIG. 1B includes a single data bus 30 which ties together all of the elements of the general purpose computer 10, there is no requirement that there be a single communication bus which connects the various elements of the general purpose computer 10. For example, the CPU 12, RAM 18, ROM 22, and graphics co-processor might be tied together with a data bus while the hard disk 20, modem 26, keyboard 24, display monitor 14, and cursor control device are connected together with a second data bus (not shown). In this case, the first data bus 30 and the second data bus could be linked by a bi-directional bus interface (not shown). Alternatively, some of the elements, such as the CPU 12 and the graphics co-processor 28 could be connected to both the first data bus 30 and the second data bus and communication between the first and second data bus would occur through the CPU 12 and the graphics co-processor 28. The methods of the present invention are thus executable on any general purpose computing architecture, but there is no limitation that this architecture is the only one which can execute the methods of the present invention.

Various visualization and analysis application may be run on the illustrative general purpose computer 10. For example, BioImage and BioPSE Power App is a visualization and analysis application developed by the University of Utah that may run on the computer 10. The software programs explore scalar data sets such as medical imaging volumes. In operation, the user chooses an input data set. BioImage supports a variety of different industry standard formats including DICOM and Analyze. For example, a dental data set containing a single tooth may be loaded into these programs.

After the data is loaded, the illustrative software program permits the user to resample, crop, histogram or median filter the data. Using a cropping filter permits visually removing the excess data from the borders of the volume. The GUI permits the user to explore the data volume in both 2-D and 3-D using the rendering panes in the software.

The software also permits slice views wherein the user can change slices and can adjust the contrast and brightness of the data. Yet another feature of BioImage is the volume rendering engine. From the volume rendering tab, the user turns on the direct volume rendering visualization. The volume rendering algorithm uses a transfer function to assign color and opacity based on both data values and gradient magnitudes of the volume. Thus, the interface between the dentin and pulp of the tooth may be colored differently. The dentin is a calcified tissues of the body, and along with enamel, cementum and pulp us one of the four major components of teeth. Pulps is the part in the center of a tooth make up of living soft tissue and cells called odontoblasts.

Figure 1C:
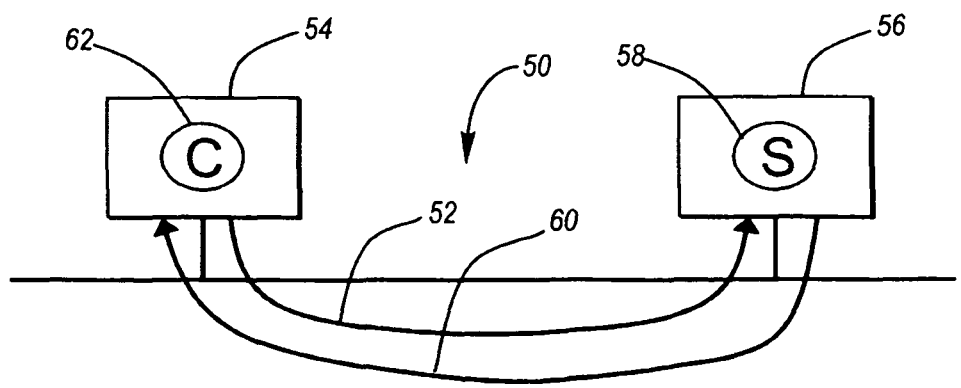
FIG. 1C is an illustrative client-server system.

Alternatively, the methods described herein may use a client/server architecture which is shown in FIG. 1C. It shall be appreciated by those of ordinary skill in the art that the client/server architecture 50 can be configured to perform similar functions as those performed by the general purpose computer 10. In the client-server architecture communication generally takes the form of a request message 52 from a client 54 to the server 56 asking for the server 56 to perform a server process 58. The server 56 performs the server process 58 and sends back a reply 60 to a client process 62 resident within client 54. Additional benefits from use of a client/server architecture include the ability to store and share gathered information and to collectively analyze gathered information. In another alternative embodiment, a peer-to-peer network (not shown) can used to implement the methods described herein.

In operation, the general purpose computer 10, client/server network system 50, or peer-to-peer network system execute a sequence of machine-readable instructions. These machine readable instructions may reside in various types of signal bearing media. In this respect, one aspect of the present invention concerns a programmed product, comprising signal-bearing media tangibly embodying a program of machine-readable instructions executable by a digital data processor such as the CPU 12 for the general purpose computer 10.

It shall be appreciated by those of ordinary skill that the computer readable medium may comprise, for example, RAM 18 contained within the general purpose computer 10 or within a server 56. Alternatively, the computer readable medium may be contained in another signal-bearing media, such as a magnetic data storage diskette that is directly accessible by the general purpose computer 10 or the server 56. Whether contained in the general purpose computer or in the server, the machine readable instructions within the computer readable medium may be stored in a variety of machine readable data storage media, such as a conventional "hard drive" or a RAID array, magnetic tape, electronic read-only memory (ROM), an optical storage device such as CD-ROM, DVD, or other suitable signal bearing media including transmission media such as digital and analog and communication links. In an illustrative embodiment, the machine-readable instructions may comprise software object code from a programming language such as C++, Java, or Python.

Figure 2A:
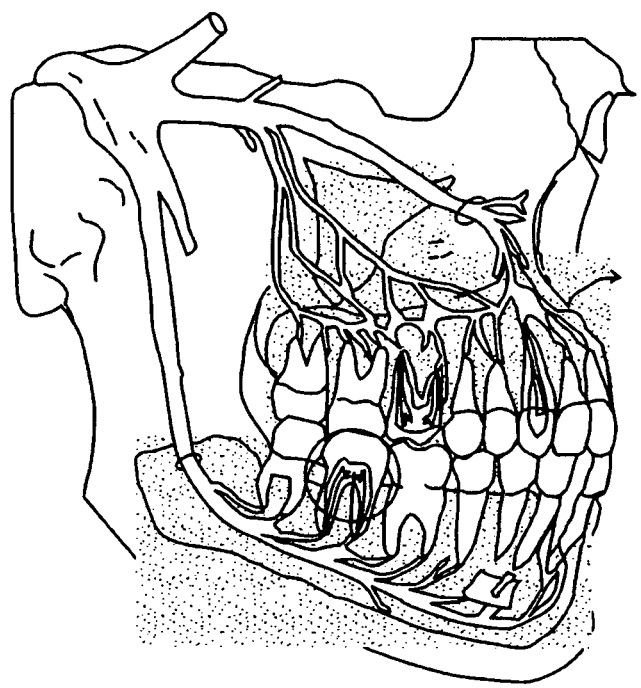
FIG. 2 is an illustrative raw image.
Figure 2B:
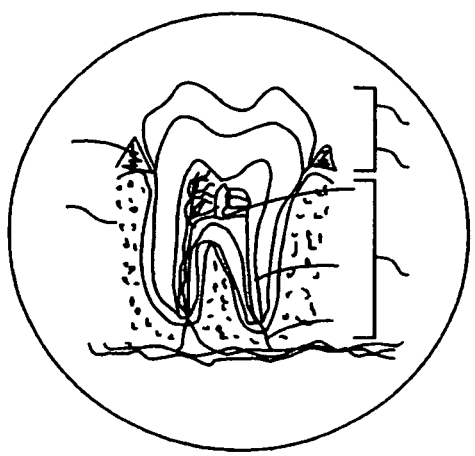

Referring to FIG. 2 there is shown an illustrative raw image of a mouth and a tooth. In general, FIG. 2 provides a visual aid of the basic anatomy of the mouth and the tooth similar to what may be generated using the illustrative i-CAT imaging system described above. This visual aid has many limitations, namely, the multiple objects in the image have not been identified. Additionally, the image is essentially a raw image that has not been standardized using some type of calibrated sample.

Figure 3:
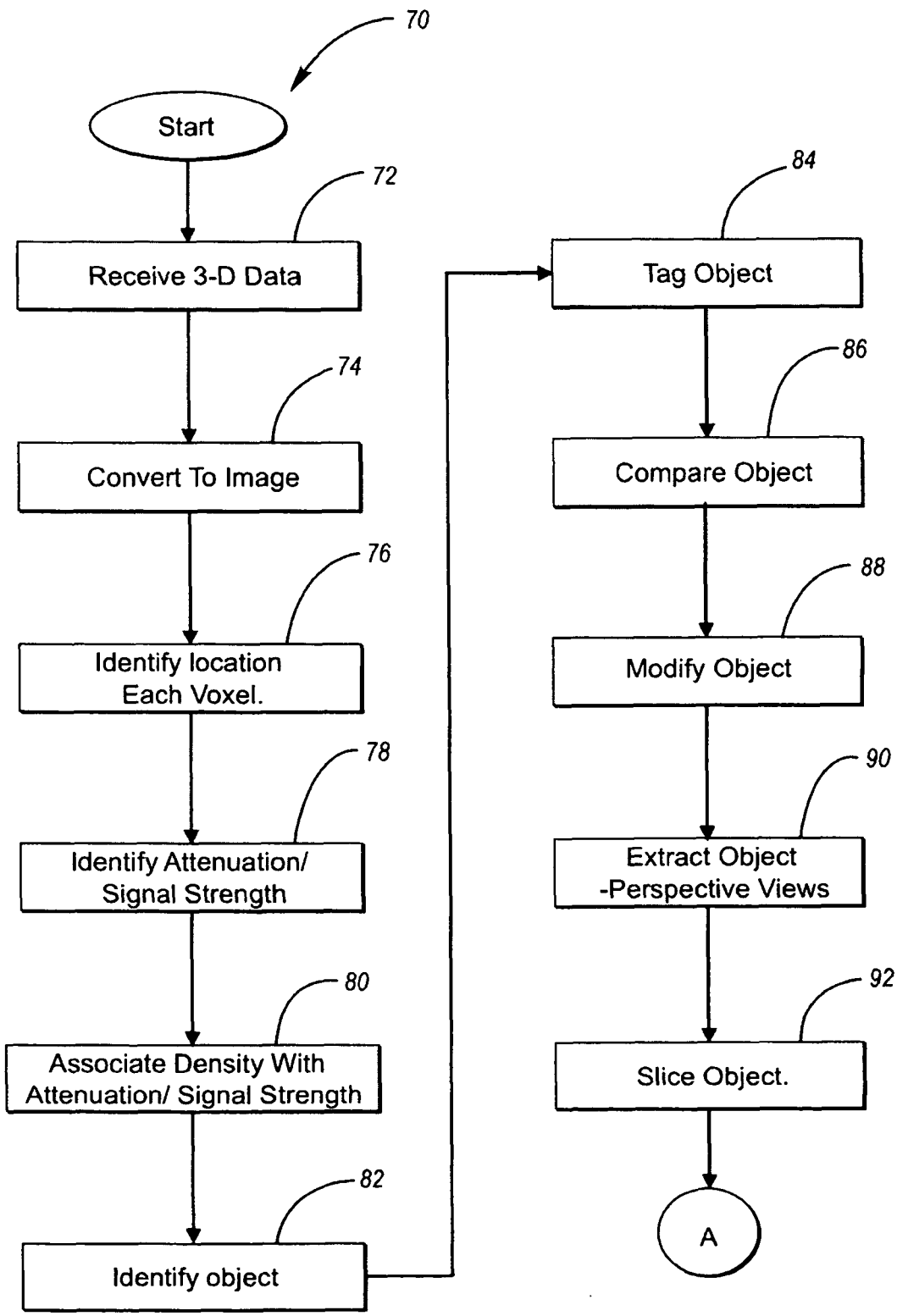
FIG. 3 is an illustrative object identification flowchart.

Referring to FIG. 3 there is shown an illustrative flowchart of a method for visualizing objects in a 3-D image 70. The illustrative method 70 for visualizing a 3-D medical image comprises receiving a plurality of high resolution 3-D medical data at block 72 that are generated using a tomography technique, e.g. computed tomography (CT) scans. By way of example and not of limitation, the method for visualizing a dental image comprises receiving a plurality of high resolution 3-D dental data associated with a patient's mouth that is generated using x-ray tomography.

The high resolution 3-D data received at block 72 includes a standard for calibration purposes. For example, with respect to CT scans, the standard may have a particular density that can be associated with a bone density. The standard is composed of a material that can be associated with the bone density of an illustrative tooth. The standard may placed adjacent to the patient and held physically or mechanically in place. Alternatively, the patient may place the standard in the mouth and bite the standard.

The method then proceeds to block 74 where the high resolution data is converted into an image comprised of a plurality of cubic voxels. At block 76, the method proceeds to identify the location for each cubic voxel. The method then proceeds to identify a degree of attenuation for the voxels at block 78. Attenuation is the reduction in amplitude and intensity of a signal.

At block 80, the method associates a common density with the degree of attenuation. The method also associates the degree of attenuation for the standard with the previously determined standard density related to block 72. For example, the degree of attenuation for each voxel is associated with at least one of a plurality of common bone densities.

The method then proceeds to block 82 that identifies an object by combining the voxels having the common density and determines an initial shape for the object. By way of example and not of limitation, the identifying of the object may comprise comparing the initial shape of the object to a standard shape. The common density may also be modified by a user, thereby resulting in the object having a different shape. For example, the 3-D data may be dental data and the common density is a bone density associated with teeth, mouth, or jaw. By way of example and not of limitation, the method then proceeds to generate dental objects by combining voxels having one of the common bone densities. The boundaries for each dental object are also determined. Various opportunities may be presented where each dental object is compared to a standard shape to confirm identification of each dental object.

The method then proceeds to block 84 where at least one object is then tagged for further analysis 78. For example, the tagged objects in the tooth may be associated with a "metatag" so that each object can be quickly identified and viewed. A "metatag" as used herein refers to a "tag" that is associated with each object, wherein the "tag" is searchable and is used to provide a structured means for identifying object so that the "tagged" object or objects can be viewed. The tagged object may then be extracted for further analysis. The extracted object may then be viewed using a plurality of different perspectives. The tagged and extracted object can then be viewed by slicing the object at desired locations. An illustrative object may be a particular tooth object, an enamel object, a dentin object, a pulp object, a root object, a nerve object, or any other such dental object associated with mouth and jaw. The plurality of objects may also be identified such as teeth objects, a plurality of nerve objects, and a plurality of bone objects. More generally, a plurality of objects may also be identified by combining the voxels having one of a plurality of different common densities and by determining the boundaries for each object.

At block 86, each of the objects is then compared to a standard shape, and each of the objects is then tagged to permit one or more objects to be combined. The plurality of objects may also be identified such as teeth objects, a plurality of nerve objects, a plurality of bone objects, or any other such object.

The flowchart also describes modifying the shape of at least one object in a scanned 3-D medical image at block 88. After the method proceeds to tag a first object and a second object, a common boundary between the first object and the second object is identified. The common boundary is configured to identify a change in bone density between the first object and the second object. The method permits a user to modify the common boundary by permitting the user to modify the apparent bone density of the first object. The method also provides for coloring each voxel according to each of the bone densities.

The common boundary spans a relatively broad area when there is little change in bone density between the first object and the second object. The method also permits evaluating a plurality of standard shapes when generating the first object and the second object. For example, each of the plurality of objects may have a plurality of tags, in which each tag may be extracted from the image as represented by block 90. By way of example and not of limitation, the first object is tagged as a first tooth and the second object is a second tooth. In another illustrative example, the first object and said second object is selected from a group consisting of a tooth object, an enamel object, a dentin object, a pulp object, a root object, a nerve object, a plurality of teeth objects, a plurality of nerve objects, or a plurality of bone objects. Additionally, the method 70 also supports performing imaging operation such as slicing objects as represented by block 92 and described in further detail below.

In operation, the method involves known physiologies discovered by the method above and supports analyzing relevant materials. After a 3-D DICOM file is converted to 3-D volumetric image, if the process has not already been completed, the volume is oriented according to axes, body portion contained, scale, etc. Object identification may be performed as a function of common densities, density transitions, and known or standard shape similarities. A map of the objects can then be created and displayed.

The systems and method described may be applied to non-specific objects, tissue identification by density, adjacent material, and general location. Margin (junction) shape determination, specific material shape (object) determination based on material profile, and cataloging of same may also be performed. For example, the identification of objects, passageways, etc. (e.g. teeth, nerve canals, implants, vertebrae, jaw, etc.) is performed. The objective is to identify recurring examples of similar objects such as teeth, and to catalog their identification, both by normative standards and by reference to statistically compiled identifiers and shape.

Figure 4A:
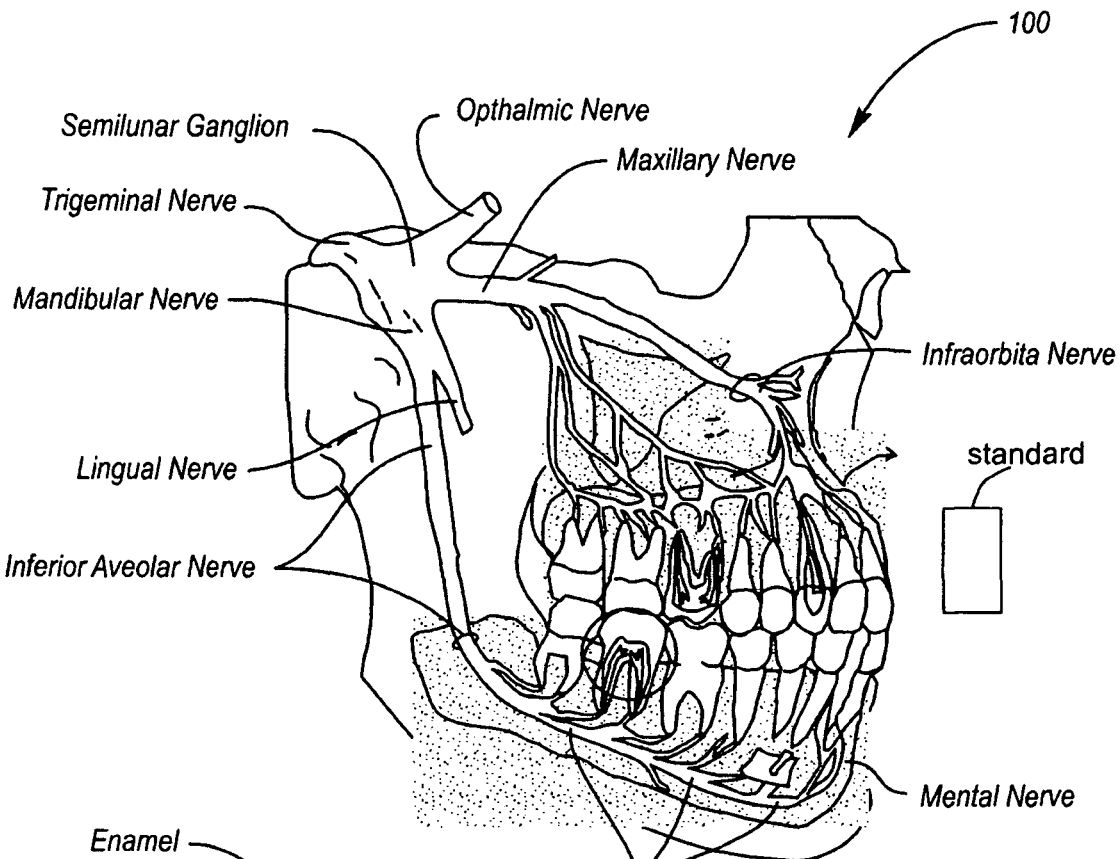
FIG. 4A is an illustrative drawing showing jaw object identification.

Referring to FIG. 4A there is shown an illustrative drawing 100 with dental and jaw object identification. As presented, the tagged objects in the tooth are associated with a "metatag" or "searchable tag" so that each object can be quickly identified and viewed. A variety of soft tissues objects such as nerve objects are shown. The nerve objects refer to sensitive tissue in the pulp of a tooth, or any bundle of nerve fibers running to various organs in the body. Additionally, a standard 102 for calibration purposes is shown. By way of example and not of limitation, these nerve objects are typically identified using MRI or CT scans.

Figure 4B:
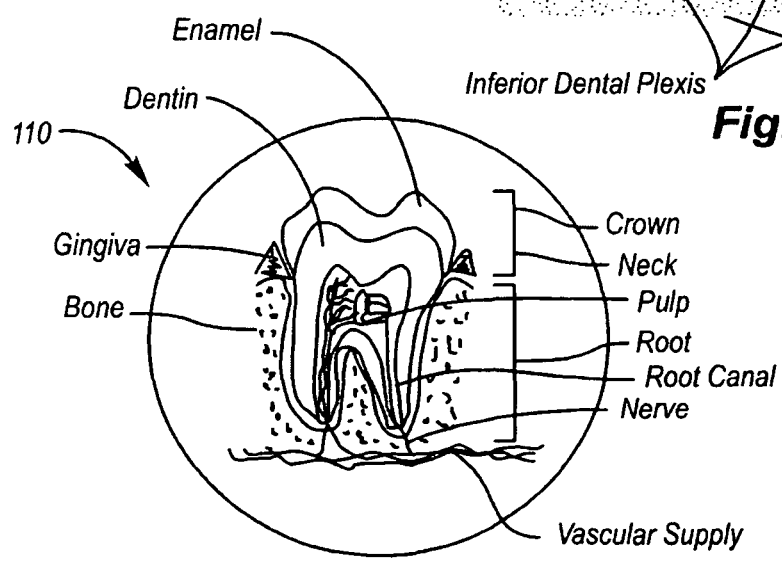
FIG. 4B is an illustrative drawing showing tooth object identification.

Referring to FIG. 4B there is shown an exploded view of a third molar tooth object 110, which is identified using the systems and methods described herein. The tooth is a set of hard, bone-like structures rooted in sockets in the jaws of vertebrates, typically composed of a core of soft pulp surrounded by a layer of hard dentin that is coated with cementum or enamel at the crown and used for biting or chewing foods or as a means of attack or defense. The tooth object is composed of a variety of different objects. One such object is an enamel object which is the hard, calcareous substance covering the exposed portion of a tooth. Another object is dentin, which is the main, calcareous part of a tooth, beneath the enamel, and surrounding the pulp chamber and root canals. The pulp object is the soft tissue forming the inner structure of a tooth and containing nerves and blood vessels. The root object is the embedded part of an organ or structure such as a tooth, or nerve, and includes the part of the tooth that is embedded in the jaw and serves as support. The root canal objects refers to the portion of the pulp cavity inside the root of the tooth, namely, the chamber within the root of the tooth that contains the pulp. The Gingiva or Gum object is the firm connective tissue covered by mucous membrane that envelops the alveolar arches of the jaw and surrounds the neck of the teeth. The neck object is the constriction between the root and the crown and can also be referred to as the Cemental-Enamel-Junction.

Figure 5:
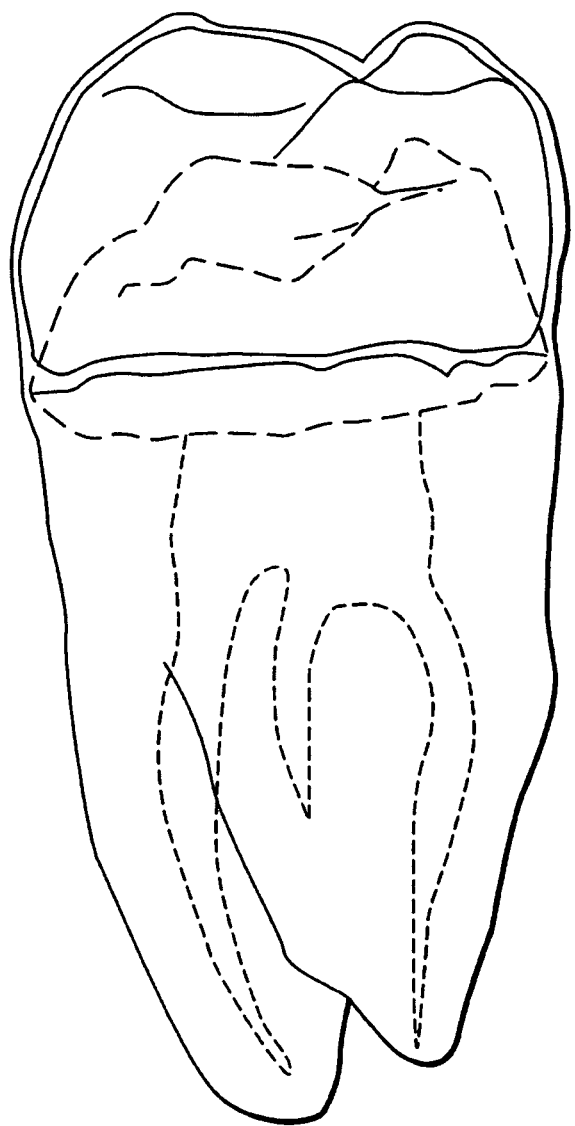
FIG. 5 is an illustrative 3-D image of a tooth object.
Figure 6:
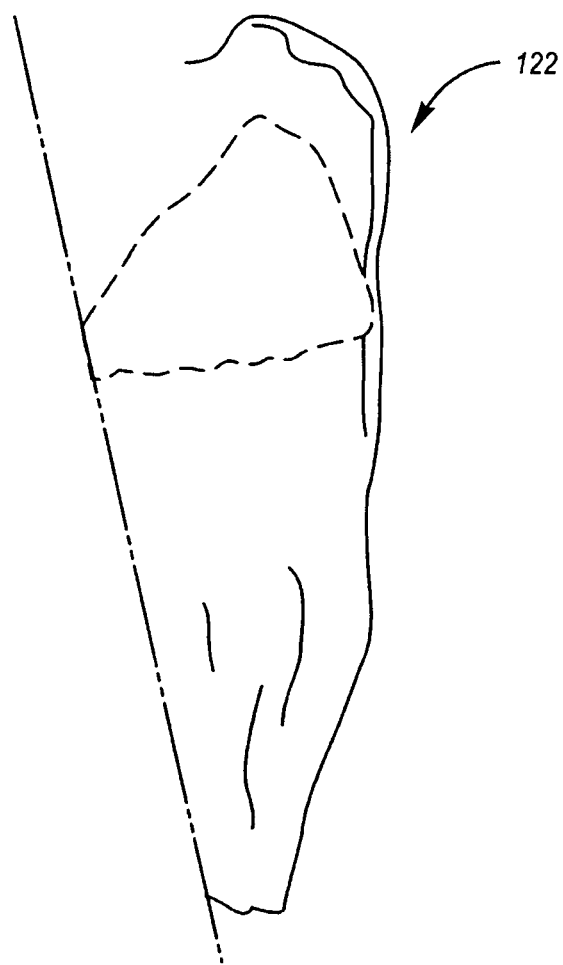
FIG. 6 is an illustrative first slice of the tooth object in FIG. 5.
Figure 7:
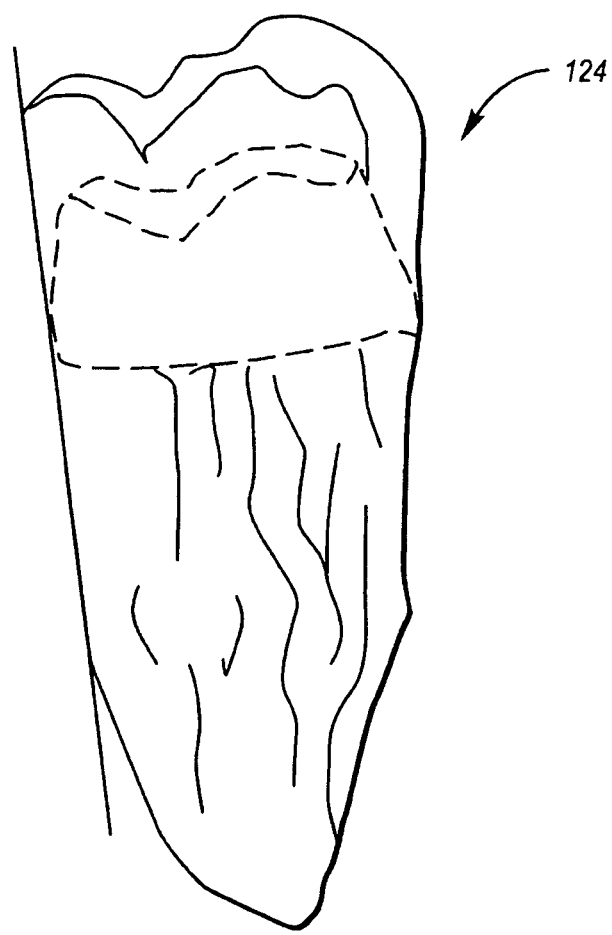
FIG. 7 is an illustrative second slice of the tooth object in FIG. 5.
Figure 8:
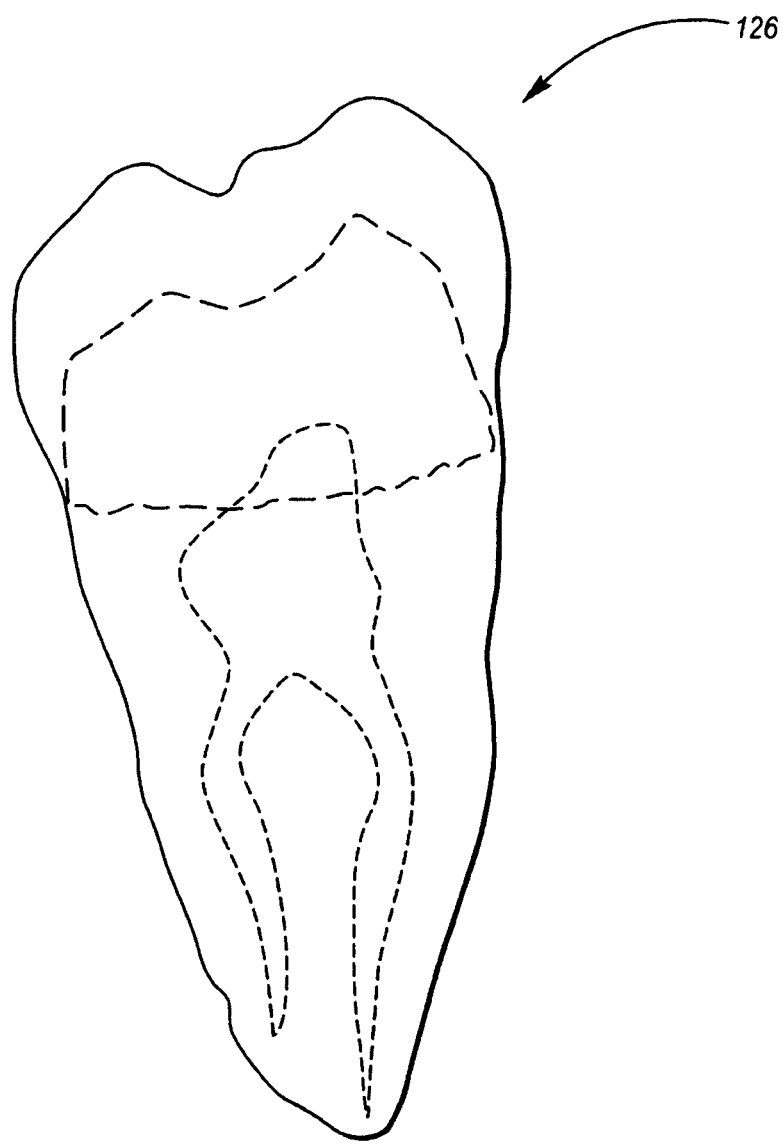
FIG. 8 is an illustrative third slice of the tooth object in FIG. 5.

Referring to FIG. 5 there is shown an illustrative 3-D image of an illustrative tooth object 120. The tooth object 120 comprises each of the objects described above such as the enamel, dentin and pulp. A variety of different slices of the 3-D image are presented. For example FIG. 6 provides an illustrative first slice 122 of the tooth object in FIG. 5. FIG. 7 provides an illustrative second slice 124 of the tooth object in FIG. 5, and FIG. 8 is an illustrative third slice 126 of the tooth object. Each of these drawings depict that the tagged objects can be "sliced" to provide a clearer view of the particular tooth. This slicing process may also be used for anomaly detection as described below.

Figure 9:
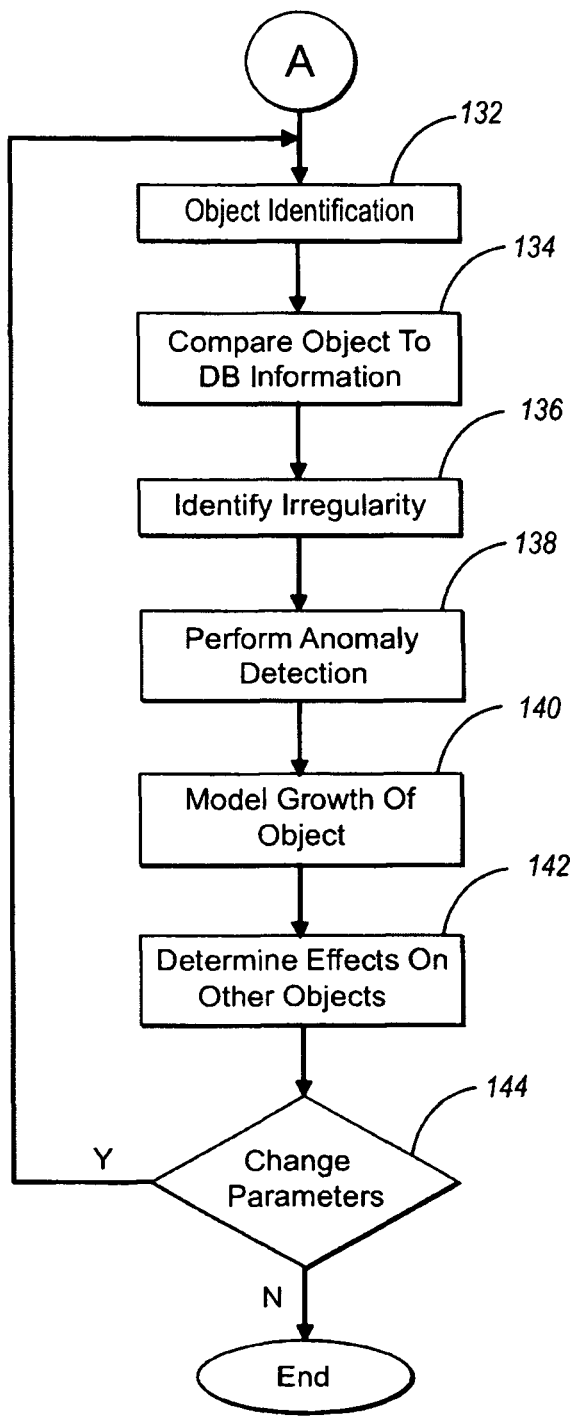
FIG. 9 is an illustrative flowchart for anomaly detection and for modeling growth rates.
Figure 10A:
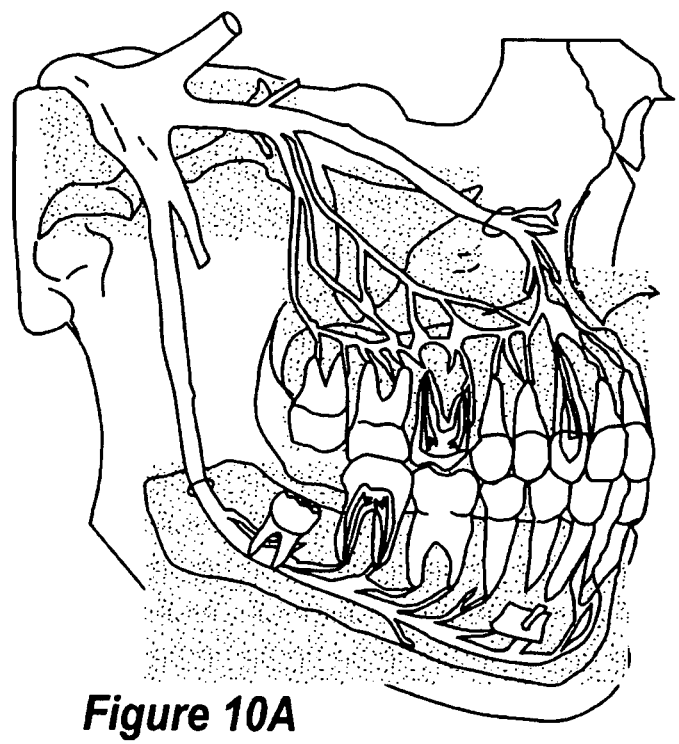
FIGS. 10A and 10B shows a normal orientation for a wisdom tooth.
Figure 10B:
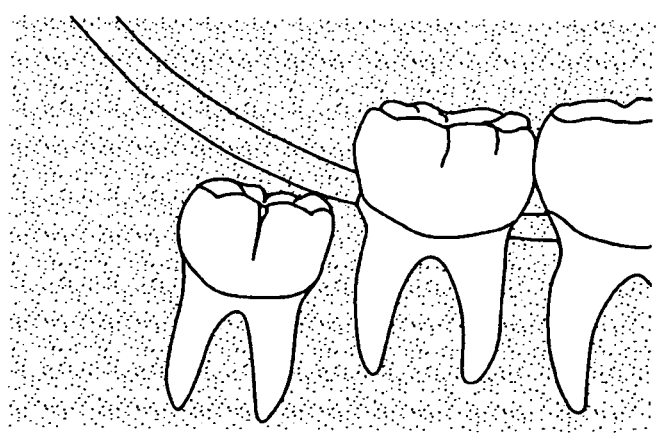

Referring to FIG. 9 there is shown an illustrative flowchart for anomaly detection and for modeling growth rates that is a continuation of the flowchart in FIG. 3. An anomaly is a deviation or departure from a normal, or common order, or form, or rule, and is generally used to refer to a substantial defect. An "irregularity" is distinguishable from an anomaly since "irregular" simply means lacking symmetry, evenness, or having a minor defect. The flowchart describes a method for identifying anomalies in a scanned 3-D dental image. The method accesses a database 206 (shown in FIG. 1A) having a plurality of data fields related to location for a plurality of teeth, a plurality of locations for each section of tooth, a plurality of standard shapes associated with the teeth, a plurality of standard shapes associated with each of the sections of tooth, and a plurality of bone density data for each section of tooth.

As previously described in FIG. 3, a 3-D image having a plurality of cubic voxels is generated, and the location for each voxel is identified. For the illustrative example described herein, the method then proceeds to identify a signal strength for each cubic voxel, and associates the signal strength for each voxel with the bone density data. Signal strength refers to the total amount of power of RF received by the receiver. This is divided into useful signal, referred to as EC/IO, and the noise floor.

The method at block 92 performs object identification at block 132 where an illustrative first object is generated by combining a first grouping of voxels having a first bone density. At block 134, the illustrative first object is compared to objects in the database 206 (shown in FIG. 1A). The method then proceeds to identify irregularities at block 136. At block 138, anomalies are identified after comparing the first object to one or more fields in the database 206. The database comprises a plurality of normative standards and statistical standards for anomaly detection that distinguished between anomalies and irregularities.

The anomaly detection at block 138 may also comprise generating a plurality of other objects and tagging the objects so that one or more objects may be combined. The method may then proceed to identify one or more anomalies associated with the plurality of objects. For example, the method supports identifying one or more anomalies associated with at least one object that is tagged as a tooth object, in which the tooth object further comprises a plurality of tagged objects selected from a group consisting of an enamel object, a dentin object, a pulp object, a root object, and a nerve object.

The method the proceeds to block 140 and performs the process of mathematically modeling growth rates. Although the illustrative example of teeth is described herein, teeth are not the only objects that grow and it shall be appreciated by that the systems and methods described herein may be used to model bone growth and bone decay in general. Growth rate projections may be based on such parameters as age, gender, height, weight, ethnicity, and other such parameters that may be valuable to mathematically modeling growth rates. Those skilled in the art shall appreciate that measurements such as bone growth are also primary indicators and are provided for illustrative purposes only.

At block 142, the relational effects resulting from having modeled the growth of a particular object are determined. Thus, the modeled growth results in changes to the local conditions, and these changes are presented to the user.

The method then proceeds to decision diamond 144 where the determination of whether to change any of the parameters described above is necessary. Therefore, modeled growth rates may be changed, thresholds for anomaly detection may be changed, and the basis for object identification may also be modified.

In operation, at least one expected growth rate is provided for at least one tooth. After the first tooth object is compared to the first tooth object data in the database, the method then proceeds to mathematically model a growth rate for the first tooth object using the expected growth rate, and modifies the location of a plurality of objects surrounding the first tooth object due to the growth of the first tooth object. The method may then proceed to identify an anomaly after comparing the first object to one or more fields in the database. Objects may then be tagged so that so that one or more objects may be combined. Anomalies may then be associated with one or more tooth objects selected from a group consisting of an enamel object, a dentin object, a pulp object, a root object, and a nerve object.

By way of example and not of limitation, anomaly detection may be performed by identifying at least one threshold for anomaly detection. The gathered data is then compared to the threshold to determine if one or more anomalies have been detected.

The potential anomaly may also be associated with a first mathematical model, which is then compared to a second "normative" mathematical model using recently extracted data. The first mathematical model may have variables that can be modified, which mirrors the ability to modify the object. The correlation between the first mathematical model and second mathematical model is determined by a correlation estimate that may be based on the concordances of randomly sampled pairs.

Additionally, the method may also provide for the use of clustering analysis. Clustering provides an additional method for analyzing the data. Spatial cluster detection has two objectives, namely, to identify the locations, shapes and sizes of potentially anomalous spatial regions, and to determine whether each of these potential clusters is more likely to a valid cluster or simply a chance cluster. The process of spatial cluster detection can separated into two parts: first, determining the expected result, secondly, determining which regions deviate from the expected result.

The process of determining which regions deviate from the expected result can be performed using a variety of techniques. For example, simple statistics can be used to determine a number of spatial standard deviations, and anomalies simply fall outside the standard deviations. Alternatively, spatial scan statistics can be used as described by Kulldorff. (M. Kulldorff. A Spatial Scan Statistic. *Communications in Statistics: Theory and Methods* 26(6), 1481-1496, 1997.) In this method, a given set of spatial regions are searched and regions are found using hypothesis testing. A generalized spatial scan framework can also be used. (M. R. Sabhnani, D. B. Neill, A. W. Moore, F.-C. tsui, M. M. Wagner, and J. U. Espino. Detecting anomalous patterns in pharmacy retail data. KDD Workshop on Data Mining Methods for Anomaly Detection, 2005.)

It shall be appreciated by those skilled in the art that the particular algorithm that is used for anomaly detection will depend on the particular application and be subject to system limitations. Thus, a variety of different algorithms for anomaly detection may be used.

An illustrative method for anomaly detection for a tooth object is shown in FIG. 10 through FIG. 14. The anomaly detection also includes modeling the crown of a tooth object and the effect the tooth object has on surrounding objects. Referring to FIG. 10A and the exploded view in FIG. 10B, there is shown a normal orientation for a wisdom tooth. In this orientation, the wisdom tooth in question has sufficient space so that there will be no horizontal impaction.

Figure 11A:
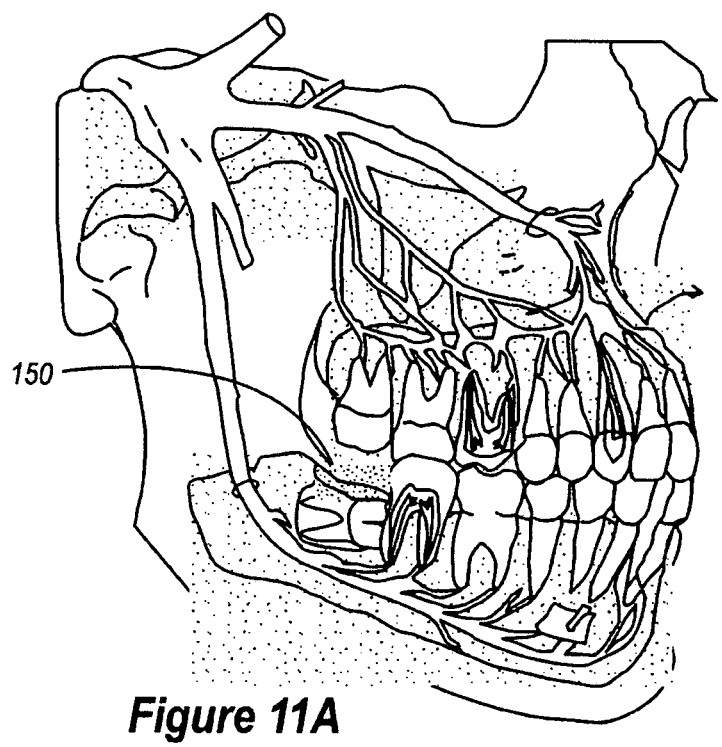
FIGS. 11A and 11B shows the beginning phase of horizontal impaction.
Figure 11B:
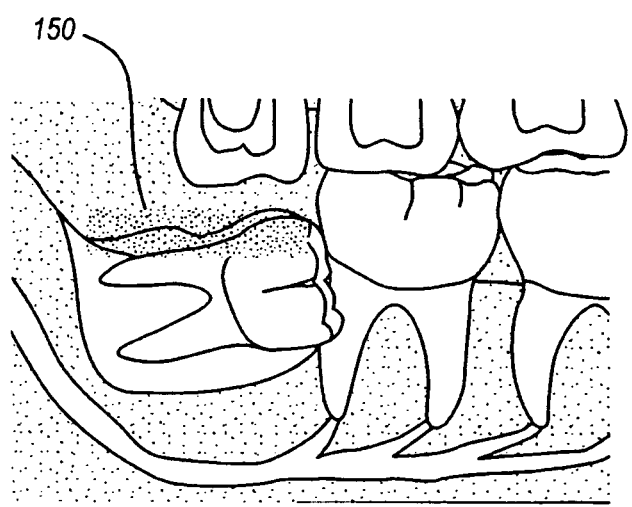

With respect to another patient, an anomaly 150 is detected in FIG. 11A and the exploded view in FIG. 11B. The anomaly reflects that this is a problem tooth, and this anomaly can immediately be brought to the physician's attention using the systems and method described herein. This image also shows the beginning phase of horizontal impaction, and the formation of a cyst. A cyst is an abnormal membranous sac containing a gaseous, liquid, or semisolid substance. Additionally, at location there is shown a dental cavity/caries that are just starting.

Figure 12A:
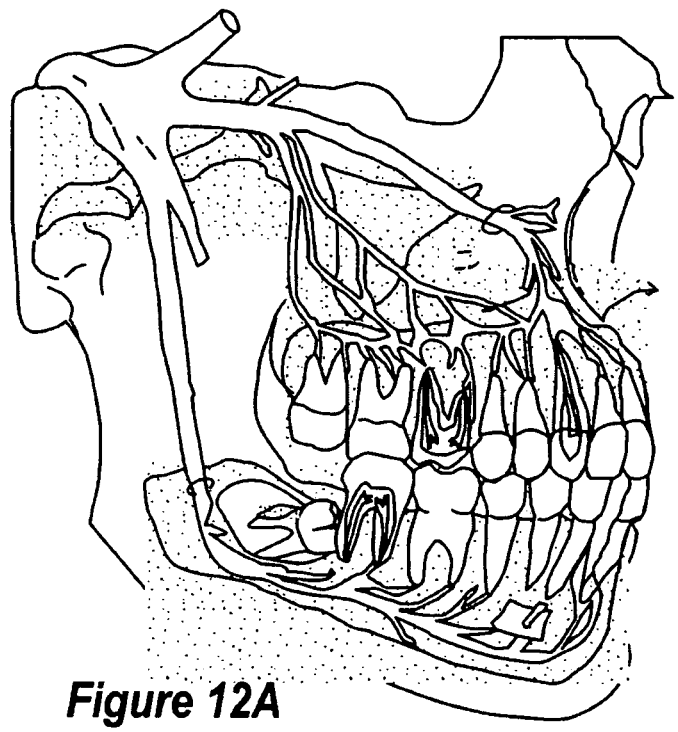
FIGS. 12A and 12B shows an illustrative example of cyst formation.
Figure 12B:
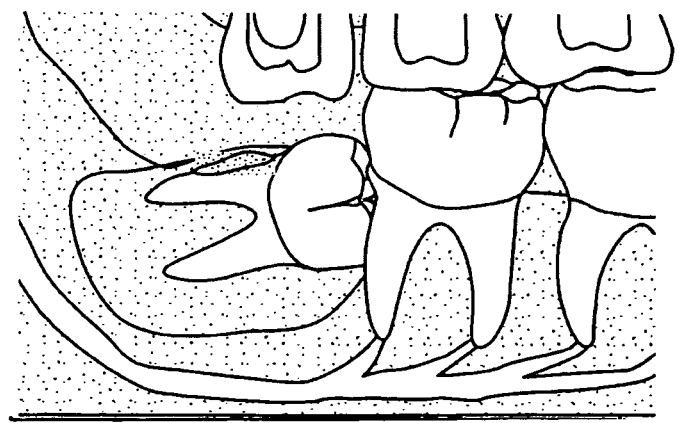
Figure 13A:
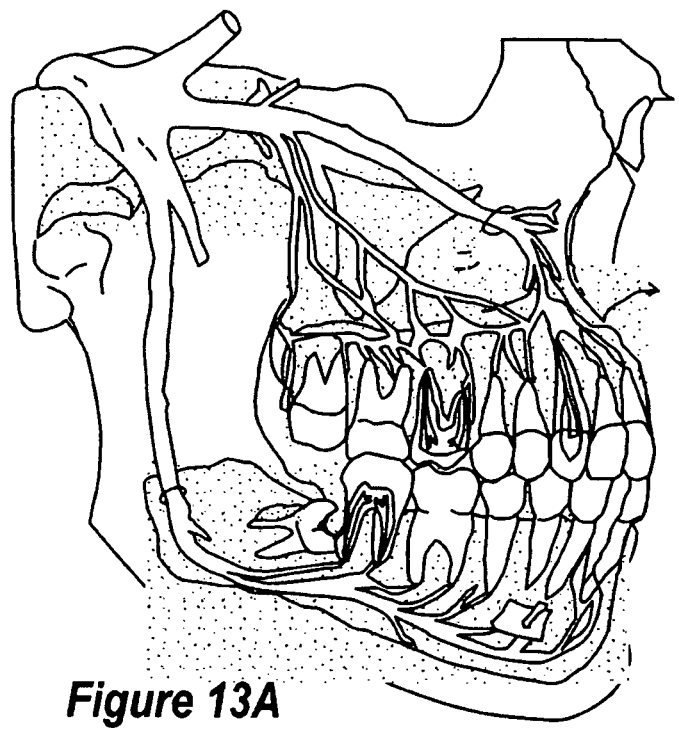
FIGS. 13A and 13B shows an illustrative example of cyst growth.
Figure 13B:
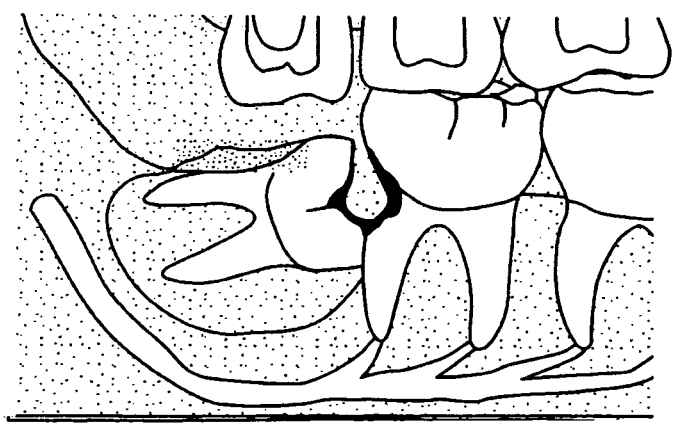
Figure 14A:
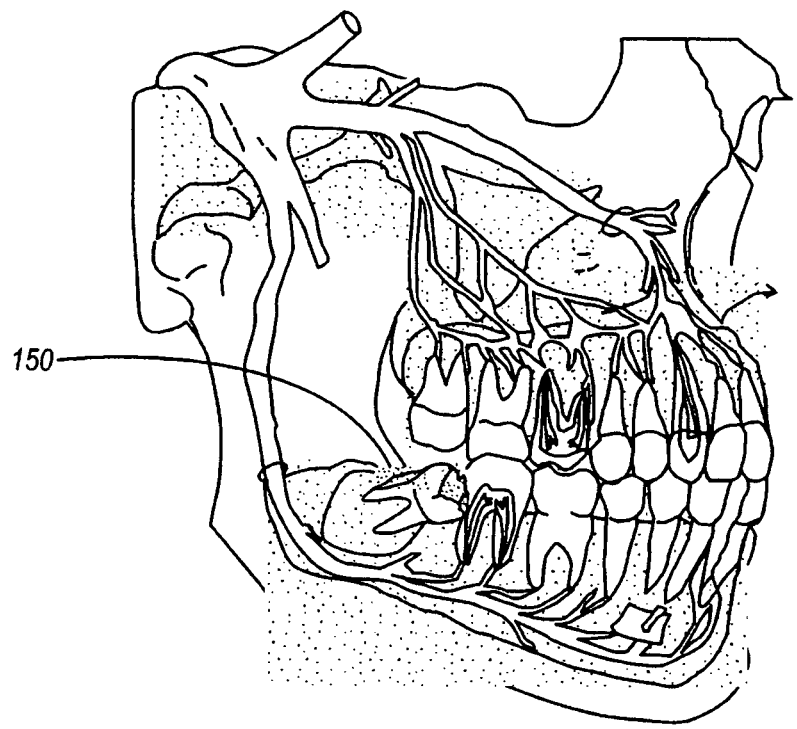
FIGS. 14A and 14B shows the resulting tooth decay and continuing cyst growth.
Figure 14B:
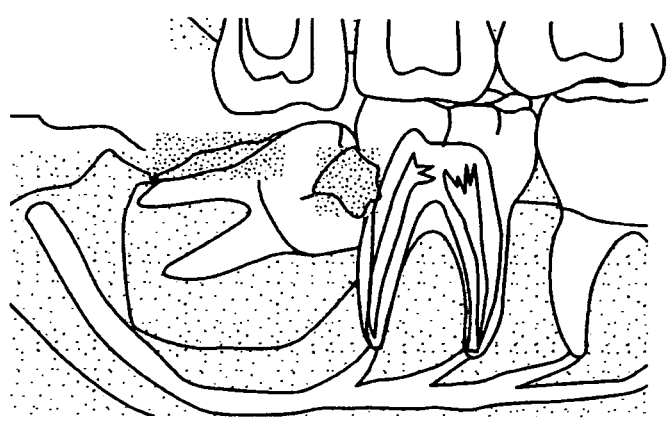

Referring to FIG. 12A and the exploded view in FIG. 12B there is shown an illustrative example of the progression, i.e. growth, of the cyst and cavity/caries after the appropriate growth models have been associated with the particular tooth 150 and the surrounding teeth. At FIG. 13A and the exploded view in 13B, there is shown the effect of cyst growth, and the initial stages of tooth decay on tooth 150. Tooth decay is an infectious, transmissible, disease caused by bacteria. The damage done to teeth by this disease is commonly known as cavities. Tooth decay can cause pain and lead to infections in surrounding tissues and tooth loss if not treated properly. The progression of the tooth decay and cyst formation is then shown in FIG. 14A and exploded view in FIG. 14B.

The illustrative systems and methods described above have been developed to assist in visualizing objects, permitting a user to modify objects, anomaly detection for objects, and for modeling growth rates associated with particular objects. It shall be appreciated by those of ordinary skill in the various arts having the benefit of this disclosure that the system and methods described can be applied to many disciplines outside of the field of dentistry. Furthermore, alternate embodiments of the invention which implement the systems in hardware, firmware, or a combination of hardware and software, as well as distributing the modules or the data in a different fashion will be apparent to those skilled in the art. Further still, the illustrative methods described may vary as to order and implemented algorithms.

Although the description above contains many limitations in the specification, these should not be construed as limiting the scope of the claims but as merely providing illustrations of some of the presently preferred embodiments of this invention. Many other embodiments will be apparent to those of skill in the art upon reviewing the description. Thus, the scope of the invention should be determined by the appended claims, along with the full scope of equivalents to which such claims are entitled.

What is claimed is:

1. A method for visualizing a dental image, comprising:
    providing a database having a plurality of data fields related to location for a plurality of teeth, a plurality of locations for each section of tooth, a plurality of standard shapes associated with the teeth, a plurality of standard shapes associated with each of the sections of tooth, and a plurality of bone density data for each section of tooth;
    receiving a plurality of high resolution 3-D dental data associated with a patient's mouth that is generated using computed tomography;
    converting the high resolution dental data into an image comprised of a plurality of cubic voxels;
    identifying a location for each cubic voxel;
    identifying a degree of attenuation for each voxel with a standard having a particular density that is associated with a bone density for a tooth, wherein the degree of attenuation is associated with reducing an amplitude and an intensity that corresponds to each voxel;
    combining voxels having a common bone density;
    determining an initial shape of the combined voxels;
    associating the initial shape of combined voxels with at least one of a plurality of common bone densities by associating the degree of attenuation of the standard having the particular density;
    generating a plurality of tooth objects selected from the group consisting of an enamel object, a dentin object, a pulp object, a root object, and a nerve object, wherein each tooth object is generated based on combining voxels having the common bone density and the initial shape of the combined voxels;
    determining a boundary for each tooth object based on the initial shape of the combined voxels;
    comparing the initial shape of the combined voxels and each tooth object boundary to a shape in the database and to the tooth bone density to confirm identification of each tooth object;
    tagging each of the tooth objects to identify the corresponding tooth object;
    providing at least one threshold to detect at least one problem tooth;
    identifying the at least one problem tooth associated with a tagged tooth object, in which the tagged tooth object is compared to the one or more thresholds in the database;
    detecting the at least one problem tooth;
    mathematically modeling growth of the at least one tooth object or bone decay for the tooth object; and
    determining the effect the problem tooth has on surrounding tooth objects.

2. The method of claim 1 further comprising extracting at least one of the tooth objects for further analysis.

3. The method of claim 2 further comprising analyzing the extracted tooth object by viewing the object using different perspectives.

4. The method of claim 3 further comprising analyzing the extracted tooth object by slicing the tooth object at desired locations.

5. The method of claim 4 further comprising identifying a common boundary between the first object and a second object, wherein a user input permits modification of the common boundary.

6. A system for visualizing a dental image, comprising:
    a database having a plurality of data fields related to location for a plurality of teeth, a plurality of locations for each section of tooth, a plurality of standard shapes associated with the teeth, a plurality of standard shapes associated with each of the sections of tooth, and a plurality of bone density data for each section of tooth;
    a plurality of high resolution 3-D dental data associated with a patient's mouth that is generated using computed tomography;
    an image comprised of a plurality of cubic voxels, wherein the image is converted from the high resolution dental data;
    a location for each cubic voxel;
    a degree of attenuation for each voxel that is compared with a standard having a particular density that is associated with a bone density for a tooth, wherein the degree of attenuation is associated with reducing an amplitude and an intensity that corresponds to each voxel;
    an initial shape for the combined voxels having a common bone density;
    a plurality of common bone densities associated with the initial shape of the combined voxels having a common bone density, wherein the degree of attenuation of the standard having the particular density;
    a plurality of tooth objects selected from the group consisting of an enamel object, a dentin object, a pulp object, a root object, and a nerve object, wherein each tooth object is generated based on combining voxels having the common bone density and the initial shape of the combined voxels;
    a processing module configured to determine a boundary for each tooth object based on the initial shape of the combined voxels, wherein the initial shape of the combined voxels and each tooth object boundary is compared to a shape in the database and to the tooth bone density to confirm identification of each tooth object, and each of the tooth objects is tagged to identify the corresponding tooth object;

at least one threshold to detect at least one problem tooth and identifying the problem tooth associated with a tagged tooth object, in which the tagged tooth object is compared to the one or more thresholds in the database;
wherein the processing module that detects the at least one problem tooth is configured to mathematically model growth of at least one tooth object or bone decay for the tooth object and determine the effect the problem tooth has on surrounding tooth objects.

7. The system of claim 6 wherein at least one of the tooth objects is configured to be extracted for further analysis.

8. The system of claim 7 wherein the extracted tooth object is configured to be analyzed by viewing the object using different perspectives.

9. The system of claim 8 wherein the extracted tooth object is configured to be analyzed by slicing the tooth object at desired locations.

10. The system of claim 9 further comprising identifying a common boundary between the first object and a second object, wherein a user input permits modification of the common boundary.

11. The method of claim 1 wherein the database comprises a plurality of normative standards and at least one statistical standard for anomaly detection.

12. The method of claim 1 wherein the standard having the particular density associated with the bone density for a tooth is placed within or near the tooth.

13. The method of claim 11 wherein the standard having the particular density associated with the bone density for a tooth is placed within or near the tooth.

14. The method of claim 6 wherein the database comprises a plurality of normative standards and at least one statistical standard for anomaly detection.

15. The method of claim 6 wherein the standard having the particular density associated with the bone density for a tooth is placed within or near the tooth.

16. The method of claim 15 wherein the standard having the particular density associated with the bone density for a tooth is placed within or near the tooth.

\* \* \* \* \*